(12) United States Patent
Konopa et al.

(10) Patent No.: US 7,697,131 B2
(45) Date of Patent: Apr. 13, 2010

(54) AUTOMATED DISPLAY QUALITY MEASUREMENT DEVICE

(75) Inventors: Kenneth D. Konopa, Mercer Island, WA (US); Paul Heydron, Everett, WA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 12/104,290

(22) Filed: Apr. 16, 2008

(65) Prior Publication Data

US 2009/0262341 A1 Oct. 22, 2009

(51) Int. Cl.
*G01N 21/00* (2006.01)
(52) U.S. Cl. ............... 356/239.2; 356/237.2; 356/239.4
(58) Field of Classification Search ... 356/237.2–237.6, 356/239.2–239.4; 348/180–189
See application file for complete search history.

(56) References Cited

U.S. PATENT DOCUMENTS

| | | | | |
|---|---|---|---|---|
| 5,349,174 A | * | 9/1994 | Van Berkel et al. ...... | 250/208.1 |
| 5,572,444 A | * | 11/1996 | Lentz et al. .................. | 348/181 |
| 5,969,756 A | * | 10/1999 | Buckley et al. ............. | 348/190 |
| 6,097,352 A | * | 8/2000 | Zavracky et al. ................ | 345/7 |
| 2007/0182964 A1 | * | 8/2007 | Den Boef et al. ........... | 356/369 |

* cited by examiner

*Primary Examiner*—Gregory J Toatley, Jr.
*Assistant Examiner*—Iyabo S Alli
(74) *Attorney, Agent, or Firm*—Dorsey & Whitney LLP (57) ABSTRACT

A method and apparatus for automating a quality assurance test conducted on display devices used for diagnostic imaging. In one embodiment, the apparatus includes an automated mechanical system for scanning a light meter over a test pattern displayed on a display device. In another embodiment, the method comprises an automated method of comparing the measured data from the light meter with an ideal image. In another embodiment, the method comprises obtaining a digital image of the test pattern displayed on the display device, and the digital image is compared with an ideal image.

13 Claims, 5 Drawing Sheets

AUTOMATED DISPLAY QUALITY MEASUREMENT DEVICE

TECHNICAL FIELD

This invention is directed toward quality assurance testing for displays, and more particularly one or more embodiments of this invention relates to an automated quality assurance test for displays that provide medical diagnostic imaging.

BACKGROUND OF THE INVENTION

Diagnostic imaging provides a technique for displaying an image of the human body to medical professionals for diagnostic purposes. Diagnostic imaging includes images produced from X-ray, computerized tomography (CT), magnetic resonance imaging (MRI), ultrasound and the like. However, many other medical imaging techniques may be used for diagnostic imaging.

Traditionally, photographic film was generally used for diagnostic imaging. Today, however, diagnostic images are often provided by a digital display device. As an example, digital display devices used in diagnostic imaging may include a cathode ray tube (CRT), Plasma monitors, liquid crystal display (LCD) and the like; however, other display devices may be used.

One concern with using digital display devices for viewing diagnostic images is knowing whether an artifact on the digital display device is from the image being displayed or an artifact in the display device itself. For example, the digital display device may have a particular defect that looks similar to a medical defect for a particular diagnostic image, thus resulting in an incorrect medical diagnosis. Defects in the display devices may be caused by pressure damage, phosphor decay or other types of damage.

Figure 1:
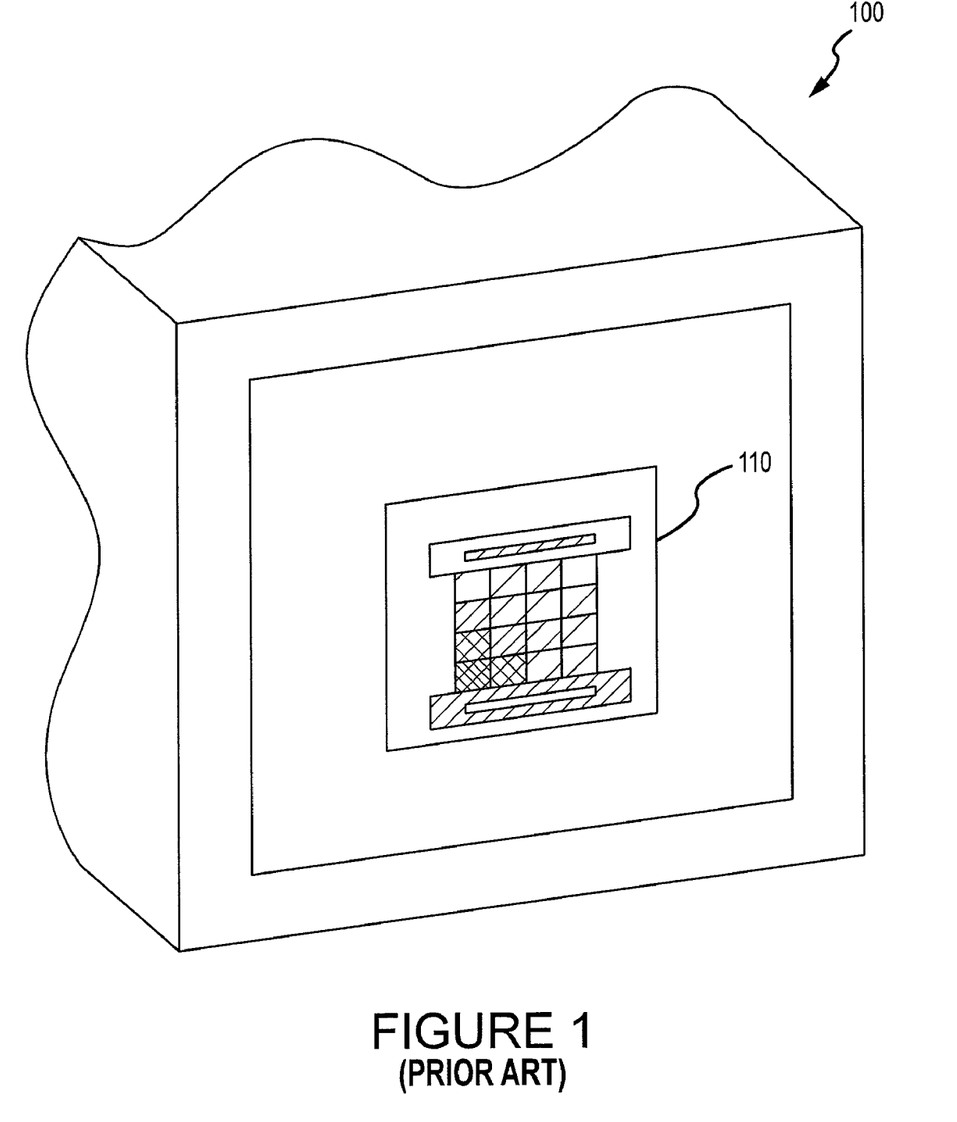
FIG. 1 is a isometric view of a test pattern being displayed on a display device in accordance with the prior art.

In order to prevent a misdiagnosis caused by artifacts in the digital display device, a quality assurance test may be performed on the display device. For instance, a quality assurance test may be performed on the device when the system is first installed or as a periodic quality assurance check. A technique that is currently being used as a quality assurance check is generating a known test pattern on the display and manually scanning the displayed test pattern with a light meter. A sample test pattern is shown in FIG. 1. In particular, FIG. 1 shows a display device 100 displaying a test pattern 110 that includes multiple levels of contrast. A light meter (not shown) is manually held in front of designated locations of the test pattern 110 to measure the alignment of the test pattern and the brightness and contrast of the display device. Contrast refers to the difference in the grayscale of black and white images. For instance, at a particular location, the grayscale value of the reading is compared with the grayscale value of the ideal image. Similarly, for color images, a hue value from the reading of the test image is compared with a hue value of the ideal image. The test results are compared with expected results. From the comparison, defective points in the display device may be detected.

The process of manually holding the light meter in front of the test pattern on the display device is laborious and time consuming. It requires a person to manually hold the light meter in front of the monitor while the test is being conducted and to manually compare the test results with the expected results, therefore, lacking precision and accuracy. Furthermore, manually holding the light meter may result in the light meter being held at multiple angles relative to the surface of the display device, rather than maintaining the light meter consistently parallel with the display device. In addition, this process results in only a portion of the display device being tested. Therefore, the results are not an accurate representation of the entire display device.

Therefore, there is a need for a faster, more accurate and repeatable method of performing a quality assurance test on the display device and automating the process of comparing the test results with the expected results.

SUMMARY OF THE INVENTION

One aspect of the present invention is directed toward an apparatus and method of performing a quality assurance test on display devices for diagnostic imaging. In one aspect of the invention, the method of performing a quality assurance test on a display device comprises displaying a test pattern on the display device, moving the light meter over the test pattern and taking readings at designated locations, providing the readings to a software application, and comparing the readings to a set of ideal data stored in the software application.

In another aspect of the invention, a display device quality assurance testing system comprises at least one mount removeably secured to the display device, a bar moveably secured to the mount, the bar being substantially perpendicular to at least one mount. In addition, a light meter is mechanically coupled to the bar, the light meter operable to move over the surface of the display device and positioned to receive light emitted from the display device, the light meter operable to measure the light emitted from the display device. Furthermore, the quality assurance testing system includes a computer system comprising a software package operable to compare the measured light from the light meter with an ideal image.

In another aspect of the invention, the method of performing a quality assurance test on a display device comprises displaying a test pattern on the display device, taking a digital image of the test pattern displayed on the display device, providing the digital image of the test pattern to a software application, and in the software application, comparing the digital image of the test pattern with an ideal image of the test pattern.

DETAILED DESCRIPTION

Embodiments of the present invention are directed toward an apparatus and method of performing a quality assurance test on display devices for diagnostic imaging. Certain details are set forth below to provide a sufficient understanding of the embodiments of the invention. However, it will be clear to one skilled in the art that various embodiments of the invention may be practiced without these particular details.

Figure 2:
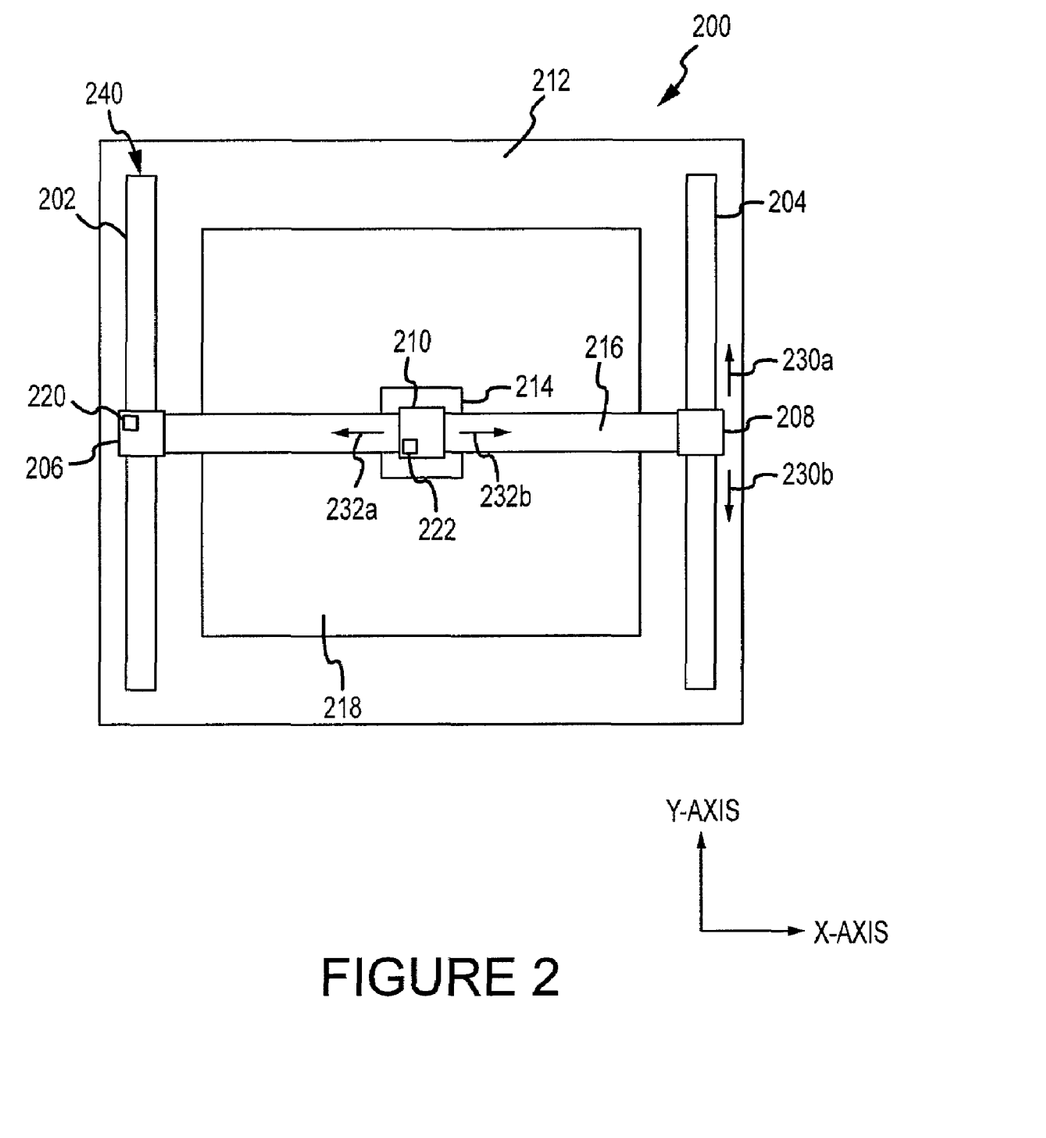
FIG. 2 a block diagram of an automated system for holding and moving the light meter over the display device according to one embodiment of the invention.

FIG. 2 is a block diagram of a mechanical system 240 for scanning a light meter 214 over a display device 200 according to one embodiment of the invention. The display device 200 includes a display frame 212 that surrounds a display screen 218, where the display screen 218 displays images. FIG. 2 shows two vertical mounts 202, 204 secured to opposites sides of the frame 212 of the display device 200. Two horizontal mounts, however, may also be used. For instance, one mount may be attached to the top of the display device 200 and the other attached to the bottom of the display device 200. As will be clear to one skilled in the art, the mounts 202, 204 may be formed of many different materials. By way of example, in one embodiment the mounts 202, 204 are made of metal, such as steal or aluminum. In another embodiment, plastic mounts are used.

As will be clear to one skilled in the art, the mounts 202, 204 may be attached to the display device 200 in any manner that allows for temporary attachment. In one embodiment, the vertical or horizontal mounts are temporarily attached to the frame 212 of the display device 200. By way of example, the mounts 202, 204 may be attached to the display device 200 by mechanical mounting, adhesive tape, such as 3M™ Command™ adhesive, suction cups or the like. The mounts 202, 204 are located on the frame 212 of the display device 200, however, in some embodiments the attachments may be located on each side of the display device 200. The mounts 202, 204 may be attached to the display device 200 to account for any curves in the display screen 218. For instance, the mounts 202, 204 may protrude beyond the surface of the display screen 218 so that the light meter is located at least some distance beyond the center of the display screen 218.

Attached to the mounts 202, 204 is a horizontal bar 216. Alternatively, if horizontal mounts are used, a vertical bar is attached to the mounts. The bar 216 is attached to the mounts 202, 204 at vertical sliders 206, 208. The vertical sliders 206, 208 are operable to move the bar 216 along the mounts 202, 204 in both directions along the mounts 202, 204 as indicated by arrows 230a, 230b. As will be clear to a person skilled in the art, the vertical sliders 206, 208 are moveably secured to the mounts 202, 204. In one embodiment, the vertical sliders 206, 208 completely wrap around the mounts 202, 204. In another embodiment, the vertical sliders 206, 208 are attached at a side of the mounts 202, 204. The sliders 206, 208 may include bearings, such as ball bearings, to facilitate a smooth motion over the mounts 206, 208. Alternatively, lubrication may be used to assist in reducing friction between the mounts 202, 204 and the vertical sliders 206, 208 and to further prevent slipping.

A light meter 214 is secured to the horizontal bar 216. The light meter 214 may be permanently or temporarily secured to the bar 216. In one embodiment, the light meter 214 is secured to the bar 216 by a holder (not shown). The holder may be attached to the horizontal slider 210 or a part of the horizontal slider 210. The horizontal slider 210 and bar 216 may have a similar design to that of the mounts 202, 204 and the vertical sliders 206, 208. These configurations will not be repeated here in the interest of brevity. As will be clear to a person skilled in the art, the light meter 214 may be temporarily secured to the holder or slider 210 by a variety of methods. By way of example, the light meter 214 may be secured to the holder or slider 210 by one or more flexible arms. Similarly, the light meter 214 may be secured to the bar by a bracket assembly (not shown), where the lighter meter 214 slides into the bracket assembly.

The light meter 214 may be any device capable of measuring light. In one embodiment, the light meter 214 is a Nuclear Associates Precision Photometer sold by the Fluke™ Corporation. A motor 220 is attached to at least one slider 206, 208 to drive the movement of the sliders 206, 208 along the mounts 202, 204 and along the Y-axis. Similarly, a motor 222 is attached to the horizontal slider 210 to drive the movement of the slider 210 along the horizontal bar 216 and along the X-axis.

Figure 3:
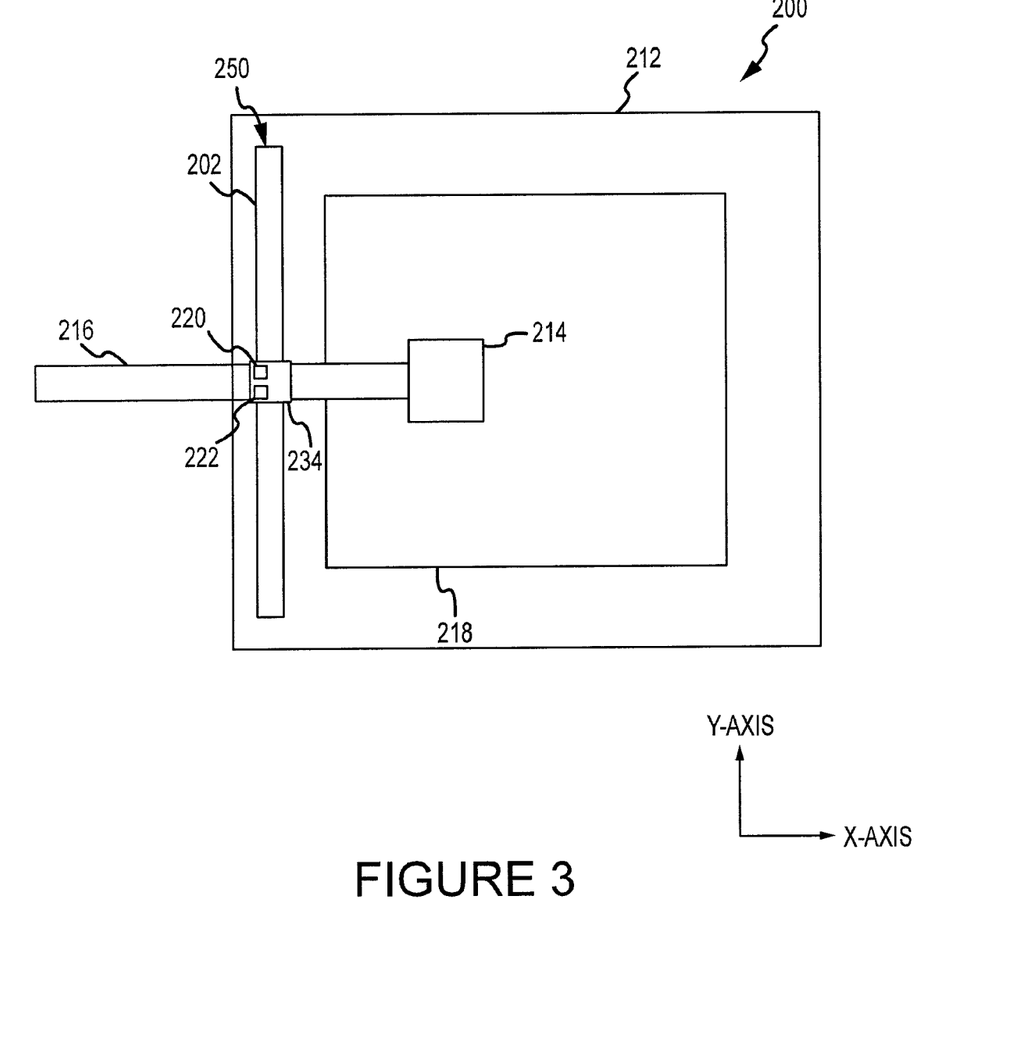
FIG. 3 is a block diagram of an automated system for holding and moving the light meter over the display device according to another embodiment of the invention.

FIG. 3 is a block diagram of a mechanical system 250 for scanning a light meter 214 over a display screen 218 according to another embodiment of the invention. Most of the components of the mechanical system 250 for scanning the light meter 214 over the display device 218 are used on the mechanical system 240 shown in FIG. 2, and they operate in the same manner. Therefore, in the interest of brevity, an explanation of their structure and function will not be repeated. The mechanical system 250 of FIG. 3 differs from the mechanical system 240 of FIG. 2 by having only one mount 202 secured to the display frame 212 and a single slider 234. The single slider 234 contains two motors 220, 222, where motor 222 drives for the X-axis and motor 220 drives the Y-axis. The slider 234 moves along the mount 202 in the same manner as the vertical sliders 206, 208 in FIG. 2 moved along mounts 202, 204. However, the slider 234 does not move in the horizontal direction. Rather, the horizontal bar 216 moves through the slider 234 and is driven by motor 222.

Figure 4:
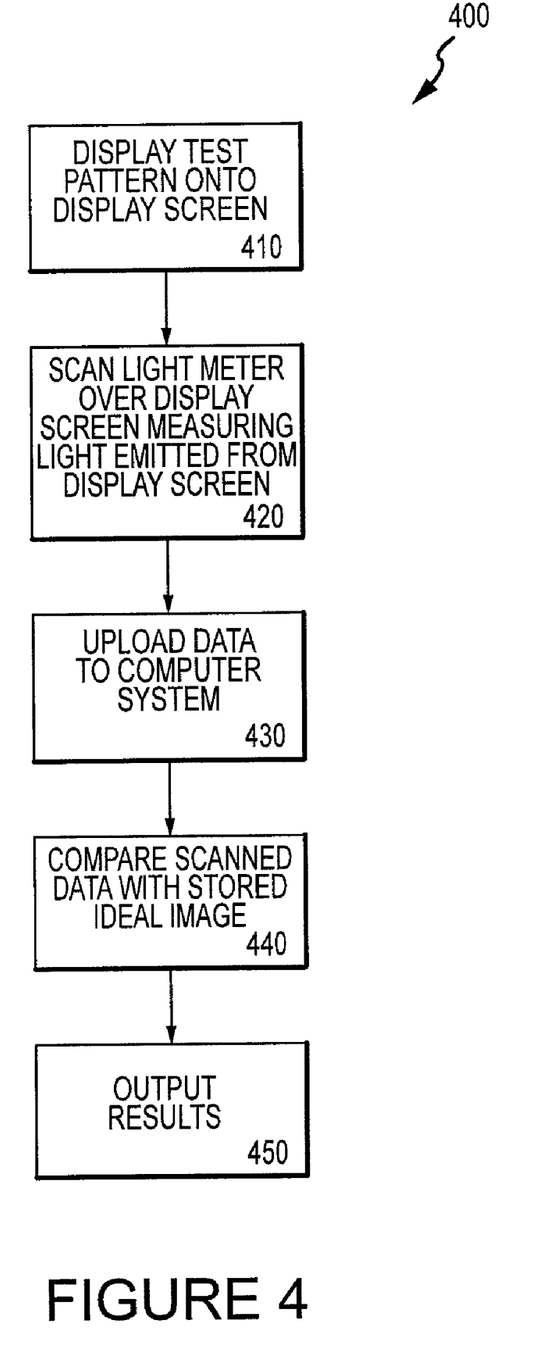
FIG. 4 flow chart illustrating a method for performing a quality assurance test on a display device according to one embodiment of the invention.

Once the automated mechanisms 240 or 250 are secured to the display device 200, a quality assurance test of the display screen 218 may be conducted. FIG. 4 is a flow chart 400 illustrating a summary of a method for performing the automated quality assurance test according to one embodiment of the invention. In step 410 a test pattern, such as the test pattern shown in FIG. 1, is displayed on the display screen; however, any known test pattern may be used. In step 420, the light meter is scanned over the display screen and measures the light emitted from the display screen. The process of scanning the light meter over the display screen may be done by one of the mechanical systems in FIGS. 2 and 3. The mechanical systems move the light meter across the display screen by moving horizontally, vertically, and/or diagonally across the display device. By using the mechanical system, the light receiving window of the light meter remains consistently parallel with the display screen of the display device. This results in more accurate readings by the light meter. Alternatively, the light meter may be manually scanned over the test pattern.

The light meter measures the light emitted from the test pattern displayed on the display screen. The light meter may measure the light emitted from a portion of the test pattern or measure the entire test pattern. In one embodiment, the light meter measures a portion of the test pattern at predetermined locations. The light meter readings are uploaded to a software package on a computer system in step 430. As will be clear to a person of ordinary skill in the art, the readings from the light meter may be transferred to the computer system through a variety of different ways. In one embodiment, the light meter may be modified to store the reading on the light meter itself and uploaded to the computer system from a portable memory device. In other embodiments, the readings are directly transferred from the light meter to the computer system, such as by a wireless or wired system. As will be clear to a person of ordinary skill the in the art, in the case of a wireless system, a wireless chip, such as a Bluetooth™ chip may be used in a wireless system. Therefore, in the interest of brevity, an explanation will not be provided.

Once the readings are uploaded to the software package, the scanned data is compared with a stored ideal image in step 340. During the comparison, the scanned data is compared to expected values from the ideal image. The comparison provides information regarding the alignment of image displayed on the displayed device. For example in one embodiment, the comparison verifies that a known line in the test pattern is straight by comparing multiple readings along the line with expected readings from an ideal image. If the display screen is curved, the software may contain a mathematical algorithm to compensate for the curvature when evaluating whether the lines are straight. In addition, the software compares the brightness and contrast values of the readings from the light meter with the expected brightness and contrast values from the ideal image. The software may allow for a specified difference in the readings and the ideal values, such as one standard deviation of known test data. This specified difference may be changed by the user in the software. The software may evaluate the uniformity of the brightness.

In step 350, the results of the comparison are provided to a user. The results may be provided to the user numerically and/or graphically. In one embodiment, the image of the test pattern is displayed indicating the areas that the scanned data does do not match the test pattern. The indicator may also include details about the results, such as a value representative of how the data point compares to the expected value of that data point or by providing an overall quality number.

Figure 5:
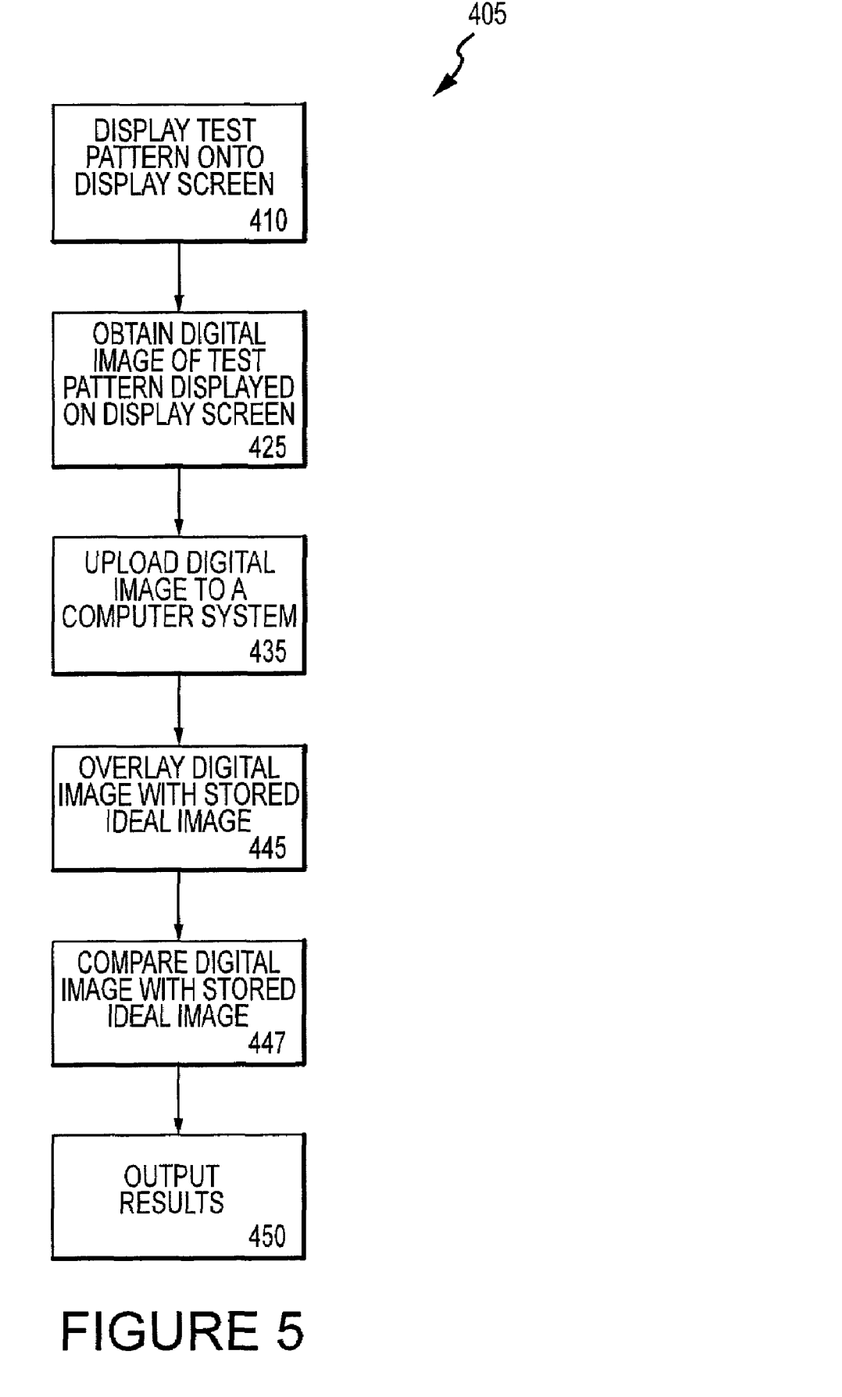
FIG. 5 is a flow chart illustrating a method for performing a quality assurance test on a display device according to one embodiment of the invention.

In another embodiment of the invention, a digital image of the test pattern may be uploaded to the software package. More particularly, a digital camera may be used to take an image of the test pattern displayed on the display device, and then the digital image is uploaded to the software package. A flow chart 405 illustrating this method is shown in FIG. 5. Step 410 is the same step as in the flow chart 400 of FIG. 4. In step 425, a digital image is taken of the test pattern displayed on the display screen. A digital camera used to take the digital image may be any type of digital camera; however, in one embodiment, the digital camera has a charge-coupled device (CCD) image sensor.

In yet another embodiment, prior to using the digital camera to take an image of the test pattern, the camera is calibrated to differentiate artifacts in the image caused by the camera from those caused by the display device. The calibration process may include a reference image taken by the digital camera that is compared to an ideal image in a software package. In one embodiment, the software package that calibrates the digital camera is the same software package used to compare the test pattern image with the ideal image. However, a separate software package may be used. In the software package, the two images may be overlayed for a point to point comparison. The results from the point to point comparison includes data that identifies differences between the reference image taken by the digital camera and the ideal reference image. The results of the comparison, the differences between the digital image and the ideal reference image, may be applied to the ideal image of the test pattern later displayed on the display screen. The results of the comparison may be represented by an image or a data set. The image or data set is representative of the differences in brightness and/or contrast between the digital reference image and the ideal reference image. The calibration data set may be represented by a data table that contains values for at least some of the locations in the point to point comparison. The values may include the brightness and/or contrast at any particular location.

Referring again to FIG. 5, at step 435, the digital image of the test pattern is uploaded to the software package. As in the calibration process, at step 445 the software package overlays the digital image of the test pattern with the ideal image of the test pattern, and at step 447 the two images are compared. This comparison process may take into account any defects detected in the digital camera during the calibration process by making adjustments to the contrast and/or brightness of the digital image based on the calibration data. This results in an adjusted digital image. Similar to the calibration process, the adjusted digital image is compared with the ideal image of the test pattern. The comparison is performed using similar methods as the calibration comparison. The software comparison is a point to point comparison, where each point is made up of multiple pixels. The point to point comparison compares fewer than the number of pixels. In one embodiment, to speed up the quality assurance test the number of pixels in each point to point comparison may be increased.

At step 450, results from the comparison are output in a similar manner as in FIG. 3 and will not be repeated in the interest of brevity. Once the results are output, a user may evaluate the results and in some cases make adjustments to the display device based on the results. For instance, if the contrast data indicates differences between the contrast of the digital test image and the ideal test image, the contrast on the display may be adjusted. Once the adjustment is made, the quality assurance test may be repeated. In another embodiment, the difference in the contrast may be represented by values and the user takes those differences into account when evaluating a diagnostic image on the display device.

Once the results of the comparison are complete, the set up of the display device may be adjusted. For instance, the contrast on the display device may be adjusted. Once any set up adjustments have been made, the quality assurance test may be repeated to evaluate the adjustment. This process may be repeated iteratively until the display set up is adjusted to a desired setting. When all quality assurance tests have been completed on the display device, the mechanical system may be removed from the display device.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

We claim:

1. A method of performing a quality assurance test on a digital display device, comprising:
   securing a light measuring device to the digital display device;
   displaying a test pattern on the digital display device;
   moving the light measuring device over the test pattern;
   using the light measuring device to measure light emitted from at least a portion of the test pattern to obtain a reading;
   providing the reading to a software application; and
   comparing the reading to a set of ideal data stored in the software application.

2. The method of claim 1 wherein the digital display device is one of cathode ray tube, plasma monitor, or liquid crystal display.

3. The method of claim 1 wherein the readings from the light measuring device are wirelessly provided to a software application.

4. The method of claim 1 wherein the act of moving a light measuring device over the test pattern at designated locations and taking readings at the designated locations comprises using an automated system for moving the light measuring device over the test pattern.

5. The method of claim 1 wherein the light measuring device is temporarily secured to the automated system.

6. The method of claim 1 further comprising adjusting the display set up based on the comparison of the readings and the ideal data stored in the software application.

7. A digital display device quality assurance testing system, comprising:
- at least one mount removeably secured to the digital display device;
- a light measuring device secured to the at least one mount, the light measuring device operable to measure the light emitted from the digital display device;
- an actuator operable to move the light meter over the surface of the digital display device so that the light measuring device can receive light emitted from the digital display device; and
- a computer system coupled to the light measuring device and the actuator, the computer system comprising a software package operable to compare the measured light from the light measuring device with an ideal image.

8. The display device quality assurance testing system of claim 7 further comprising a bar moveably secured to the at least one mount, the bar being substantially perpendicular to the at least one mount.

9. The display device quality assurance testing system of claim 7 wherein the light measuring device is removeably secured to the actuator.

10. The display device quality assurance testing system of claim 7 wherein two mounts are removably secured to opposite sides of the surface of the digital display device.

11. The display device quality assurance testing system of claim 7 wherein the mounts are removeably secured to the digital display device by one of adhesive and suction cups.

12. The display device quality assurance testing system of claim 7 wherein the light measuring device comprises a wireless chip operable to wirelessly upload the measurements from the light measuring device to the computer system.

13. The display device quality assurance testing system of claim 7 wherein the ideal image is stored in the software package.

* * * * *

UNITED STATES PATENT AND TRADEMARK OFFICE
CERTIFICATE OF CORRECTION

PATENT NO.         : 7,697,131 B2                                          Page 1 of 1
APPLICATION NO.    : 12/104290
DATED              : April 13, 2010
INVENTOR(S)        : Kenneth D. Konopa et al.

It is certified that error appears in the above-identified patent and that said Letters Patent is hereby corrected as shown below:

| Column, Line | Reads | Should Read |
|---|---|---|
| Column 2, Line 44 | "FIG. 1 is a isometric" | --FIG. 1 is an isometric-- |
| Column 2, Line 46 | "FIG. 2 a block" | --FIG. 2 is a block-- |
| Column 2, Line 52 | "FIG. 4 flow chart" | --FIG. 4 is a flow chart-- |
| Column 4, Lines 65-66 | "image in step 340." | --image in step 440.-- |
| Column 5, Line 16 | "In step 350," | --In step 450,-- |

Signed and Sealed this

Twenty-second Day of June, 2010

David J. Kappos
*Director of the United States Patent and Trademark Office*